United States Patent
Al-Rafia et al.

(10) Patent No.: US 9,543,529 B2
(45) Date of Patent: Jan. 10, 2017

(54) COMPOUNDS CONTAINING ELECTRON RICH AND ELECTRON DEFICIENT REGIONS AND THEIR USE IN ORGANIC ELECTRONIC APPLICATIONS

(71) Applicant: SABIC Global Technologies B.V., Bergen op Zoom (NL)

(72) Inventors: S. M. Ibrahim Al-Rafia, Edmonton (CA); Tate C. Hauger, Edmonton (CA); Jillian M. Buriak, Edmonton (CA); Amit K. Tevtia, Thuwal (SA); Ahmed I. Abdelrahman, Thuwal (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 14/912,253

(22) PCT Filed: Feb. 4, 2015

(86) PCT No.: PCT/IB2015/050854
§ 371 (c)(1),
(2) Date: Feb. 16, 2016

(87) PCT Pub. No.: WO2015/121775
PCT Pub. Date: Aug. 20, 2015

(65) Prior Publication Data
US 2016/0211463 A1    Jul. 21, 2016

Related U.S. Application Data

(60) Provisional application No. 61/938,296, filed on Feb. 11, 2014.

(51) Int. Cl.
| | |
|---|---|
| *H01L 51/54* | (2006.01) |
| *C09K 11/06* | (2006.01) |
| *H01L 51/00* | (2006.01) |
| *C07D 495/04* | (2006.01) |
| *C07F 7/22* | (2006.01) |
| *C08G 61/12* | (2006.01) |
| *C07F 7/08* | (2006.01) |
| *H01L 51/44* | (2006.01) |
| *H01L 51/42* | (2006.01) |

(52) U.S. Cl.
CPC ......... *H01L 51/0071* (2013.01); *C07D 495/04* (2013.01); *C07F 7/0816* (2013.01); *C07F 7/2212* (2013.01); *C08G 61/123* (2013.01); *C08G 61/126* (2013.01); *H01L 51/0068* (2013.01); *H01L 51/0069* (2013.01); *H01L 51/0074* (2013.01); *H01L 51/0094* (2013.01); *H01L 51/0097* (2013.01); *H01L 51/441* (2013.01); *C08G 2261/146* (2013.01); *C08G 2261/1412* (2013.01); *C08G 2261/164* (2013.01); *C08G 2261/226* (2013.01); *C08G 2261/3223* (2013.01); *C08G 2261/3247* (2013.01); *C08G 2261/344* (2013.01); *C08G 2261/364* (2013.01); *C08G 2261/414* (2013.01); *C08G 2261/91* (2013.01); *H01L 51/001* (2013.01); *H01L 51/4253* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 7,470,377 B2 | 12/2008 | Heeney et al. | 252/299.01 |
| 2002/0165215 A1 | 11/2002 | Lam et al. | 514/183 |
| 2007/0119496 A1* | 5/2007 | Baldo | B82Y 10/00 136/252 |
| 2007/0287842 A1 | 12/2007 | Skene | 549/50 |
| 2011/0049367 A1* | 3/2011 | Forrest | B82Y 10/00 250/338.4 |

FOREIGN PATENT DOCUMENTS

| | | |
|---|---|---|
| EP | 2041222 B1 | 12/2012 |
| WO | WO 2012162794 | 12/2012 |
| WO | WO 2013123047 | 8/2013 |

OTHER PUBLICATIONS

Qian et al. Chem. Mater. 2008, 20, 6208-6216. Date of web publication: Sep. 18, 2008.*
Kitamura et al. Chem. Mater. 1996, 8, 570-578. Year of publication: 1996.*
Ding et al., *Adv. Mater.* 24:3639-3645, 2012.
Dou et al., *Adv. Mater.* 25:825-831, 2013.
Gao et al., *ACS Nano* 6(8):7114-7121, 2012.
Gibson et al., *J. Am. Chem. Soc.* 134:539-547, 2012.

(Continued)

*Primary Examiner* — Andrew K Bohaty
(74) *Attorney, Agent, or Firm* — Norton Rose Fulbright US LLP

(57) ABSTRACT

Disclosed are semiconducting or conducting organic small molecules, oligomers, and polymers that are based on a donor-acceptor strategy featuring heavy group 16 elements (Se and Te) at the core of acceptor unit(s). The small molecules, oligomers, and polymers can have the following generic structure and can be used in areas such as organic electronic materials and devices:

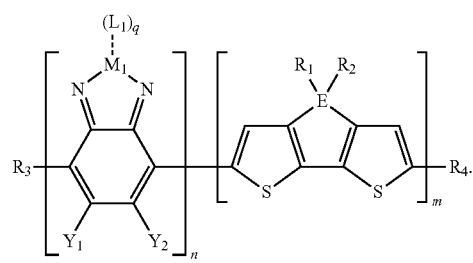

20 Claims, 3 Drawing Sheets

(56) References Cited

OTHER PUBLICATIONS

Gibson et al., *J. Phys. Chem. C* 117:16606-16615, 2013.
Hou et al., *J. Phys. Chem. C* 113:1601-1605, 2009.
International Preliminary Report on Patentability for PCT/IB2015/050854, mailed Jan. 27, 2016.
International Search Report and Written Opinion for PCT/IB2015/050854, mailed Jun. 23, 2015.
Kaur et al., *Chem. Commun.* 49:5495-5497, 2013.
Mishra et al., *Angew. Chem. Int. Ed.* 51:2020-2067, 2012.
O'Boyle et al., *J. Phys. Chem. C* 115(32):16200-16210, 2011.
Pappenfus et al., *Macromolecules* 44:2354-2357, 2011.
Rand et al., *Phys. Rev. B* 75(11):115327, 2007.
Saadeh et al., *ACS Macro Lett.* 1:361-365, 2012.
Singh et al., *J. Chem Soc., Dalton Trans.* 7:1267-1273, 1984.
Yamashita et al., *J. Mater. Chem.* 8(9):1933-1944, 1998.

* cited by examiner

COMPOUNDS CONTAINING ELECTRON RICH AND ELECTRON DEFICIENT REGIONS AND THEIR USE IN ORGANIC ELECTRONIC APPLICATIONS

CROSS REFERENCE TO RELATED APPLICATIONS

This application is a national phase application under 35 U.S.C. 371 of International Application No. PCT/IB2015/050854 filed Feb. 4, 2015, which claims benefit to U.S. Provisional Application No. 61/938,296 titled "COMPOUNDS CONTAINING ELECTRON RICH AND ELECTRON DEFICIENT REGIONS AND THEIR USE IN ORGANIC ELECTRONIC APPLICATIONS" filed Feb. 11, 2014. The entire contents of the above referenced patent applications are incorporated into the present application by reference.

BACKGROUND OF THE INVENTION

A. Field of the Invention

The invention generally concerns small molecules and related oligomers that have selenium or tellurium or both incorporated therein. These compounds have electron rich and electron deficient regions and can be used in organic electronic applications.

B. Description of Related Art

The search for more efficient and economically viable electronic devices is an ongoing process. This is especially the case for organic electronic applications (e.g., both photovoltaic and non-photovoltaic applications).

Organic photovoltaic (OPV) and non-OPV electronic devices based upon bulk heterojunction (BHJ) architectures are considered to be an ideal format to harvest radiation due to their low cost of fabrication, flexibility, and atom economic power conversion efficiency (PCE) compared to their inorganic analogues. The energy gap between the highest occupied molecular orbital (HOMO) and lowest unoccupied molecular orbital (LUMO) of organic light harvesting materials (polymers, oligomers, and small molecules) dictates their light harvesting capabilities. The electronic structure also influences the charge carrier mobility of both electrons and holes.

The use of small organic molecules in the active layer in the BHJ is being considered as an intriguing alternative to more commonly used high molecular weight organic polymer-based counterparts. Compared to conjugated polymers, small molecules offer a higher degree of control over synthetic methodology, and easier characterization, purification and solution-based processing. Although in many instances energy output from small molecule BHJ-based electronic devices is comparable to polymer-based counterparts, they still fall below the maximum theoretically predicated efficiencies of 10-12%. The development of small molecule BHJ-based devices has been slowed down due to the lack of availability of suitable organic small molecules that have the appropriate optical and electronic properties to deliver the maximum PCE. The current limitations of existing small molecules and oligomers include complex synthetic procedures and purification methods, poor solubility parameters, and minimal control over optical and electronic properties.

SUMMARY OF THE INVENTION

The present invention offers a solution to the aforementioned problems associated with current compounds that are used in electronic devices. The solution is premised on a donor-acceptor (D-A) approach when creating the small molecules or oligomers of the present invention, which can be semiconducting or conducting molecules or oligomers. In particular, the small molecules or oligomers have low band gap semiconducting properties due to the presence of a delocalized pi-electron system that has alternating electron rich (donor) and electron-deficient (acceptor) units. The use of heavy group 16 elements (Se and Te) at the core of acceptor units allows for improved light absorption properties and enhanced electronic properties, including increased charge carrier mobility. Further, the light absorption properties of the small molecules and oligomers of the present invention can be extended up to the ultraviolet and near infrared regions of solar radiation, which allows for increased efficiency as well as fabrication of visibly transparent solar cells. Additional advantages of the small molecules and oligomers of the present invention include: straight forward synthesis; scalable reaction and purification conditions; high degree of solubility in common organic solvents, thereby allowing for efficient solution-based processing during device fabrication; tunable electronic and optical properties via the presence of selenium or tellurium (or both), which allows for the formation of hypervalent coordination complexes; and photoluminescence properties.

In one embodiment of the present invention, there is disclosed a compound having the following structure:

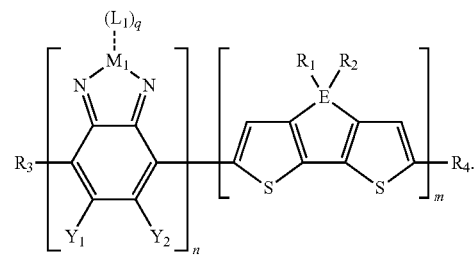

E can be C, Si or Ge. $R_1$ and $R_2$ are each independently a linear, branched or cyclic aliphatic, aryl or heteroaryl group of up to 20 carbon atoms. $R_3$ can be:

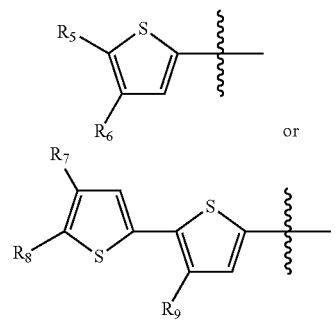

$R_4$ can be:

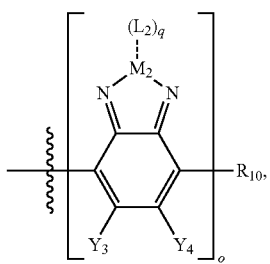

where $R_{10}$ is

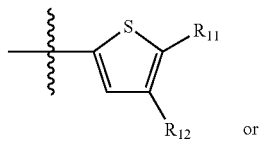

or

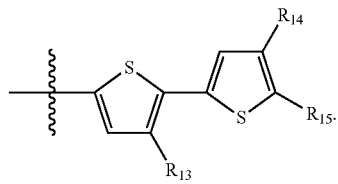

$R_5$, $R_6$, $R_7$, $R_8$, $R_9$, $R_{11}$, $R_{12}$, $R_{13}$, $R_{14}$, and $R_{15}$ are each independently H, a linear, branched or cyclic aliphatic, aryl or heteroaryl group of up to 20 carbon atoms, with the proviso that both of $R_5$ and $R_6$ are not H, both of $R_7$ and $R_8$ are not H, both of $R_{11}$ and $R_{12}$ are not H, and both of $R_{14}$ and $R_{15}$ are not H. $M_1$ and $M_2$ can each individually be Se or Te. $L_1$ and $L_2$ can each individually a coordination ligand bound to $M_1$ and $M_2$, respectively, through a coordination bond, with q being an integer from 0 to 4. In preferred aspects, $L_1$ and $L_2$ are each individually Cl, Br, I, a linear, branched or cyclic aliphatic, aryl or heteroaryl group of up to 20 carbon atoms. $Y_1$, $Y_2$, $Y_3$, and $Y_4$ can each independently be H, F, $NO_2$, CN, $N(R_{16})_2$, $OR_{17}$, $CF_3$, or $C_6H_zX_{6-z}$. Further, $Y_1$ and $Y_2$ or $Y_3$ and $Y_4$ or all can be N and are connected by a metal bridge atom to form, together with the carbon atoms to which they are attached, a 5 member ring system, or a coordination ligand (e.g., in instances where Se and/or Te are in +4 oxidation states). $R_{16}$ and $R_{17}$ can each independently be a linear, branched or cyclic aliphatic, aryl or heteroaryl group of up to 20 carbon atoms. X can be F, Cl or Br. z can be an integer from 0 to 6. n and m can each be integers from 1 to 5. o can be an integer from 0 to 5, with the proviso that when o is 0, then $R_4$ is either $R_3$ or an aromatic, hetero-aromatic, or alkyl functional group. In one particular instance, the compound can have the following structure:

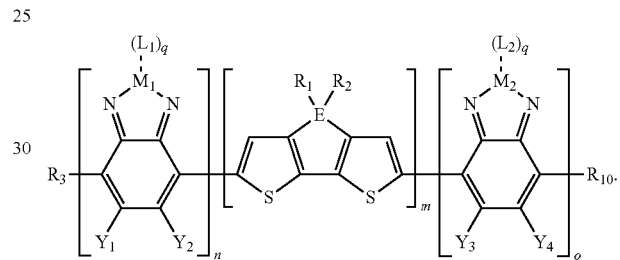

In another instance, the compound can have the following structure:

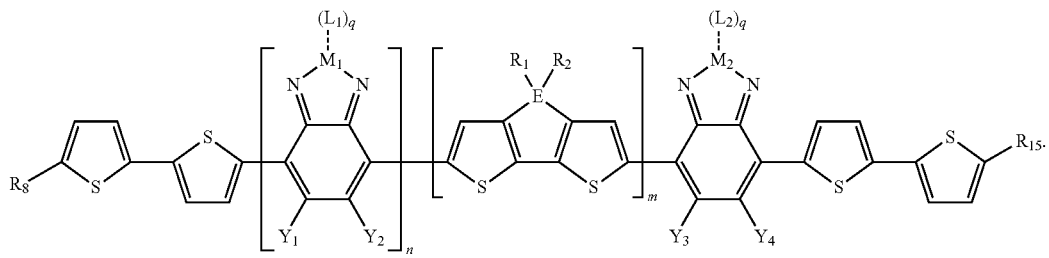

In still another aspect, the compound can have the following structure:

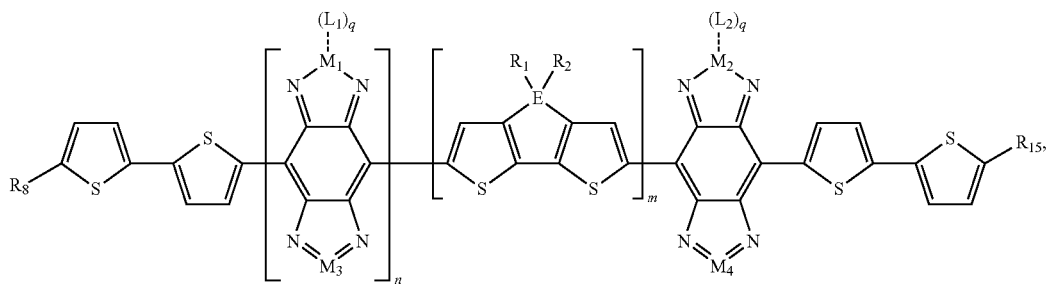

wherein $M_3$ and $M_4$ are each independently Se or Te. In yet another aspect, the compound can have one of the following structures:

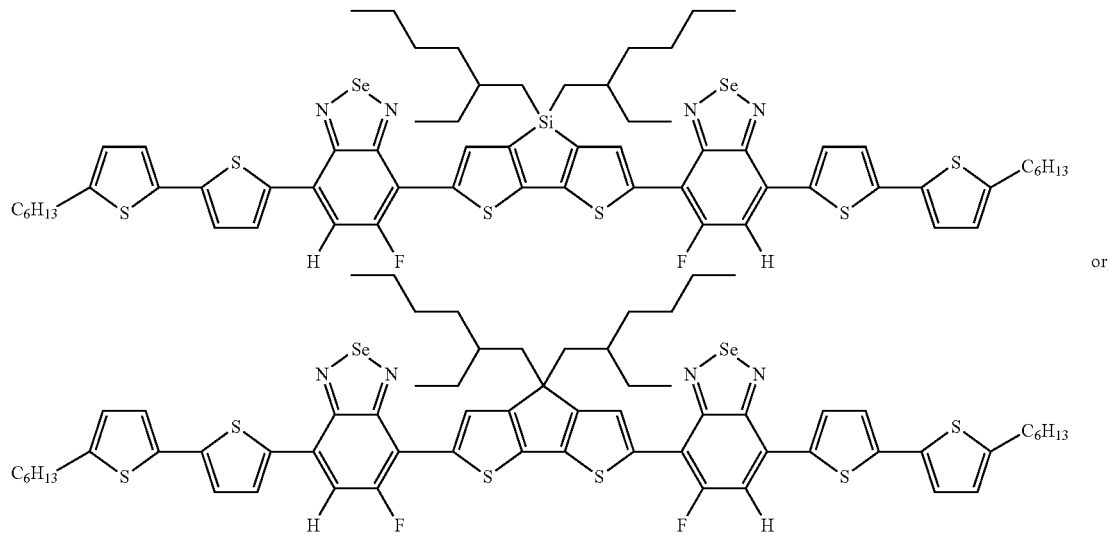

or

Any of the compounds of the present invention can be purified or isolated by techniques known to those of skill in the art (e.g., filtration, precipitation, steam distillation, distillation evaporation, sublimation, centrifugation, decantation, or the like). The purified or isolated compound can be in a dry or powdered form or can be stored within a liquid. The produced compound can be further modified with a dopant so as to enhance its p-type or n-type properties. The produced compounds can be conductive or semi-conductive compounds and can be used in such electronic applications and devices.

In another embodiment of the present invention, the compounds (e.g., small molecules, oligomers, and polymers) of the present invention can be used in electronic applications. These compounds can be used in an active layer of an electronic device. The active layer can be an organic or hybrid semiconducting or conducting layer. The device can include a substrate, the photoactive layer, and at least two electrodes, one of which is transparent, wherein at least a portion or all of the photoactive layer is disposed between said electrodes. The transparent electrode can be a cathode and the other electrode can be an anode. Alternatively, the transparent electrode can be an anode and the other electrode can be a cathode. In some instances both of the aforementioned electrodes can be transparent. In other instances, one of the electrodes can be transparent while the other is non-transparent (e.g., opaque) or reflective, such that it can reflect electromagnetic radiation such as ultraviolet light or visible light or sun light. Still further, the substrate can be opaque, reflective, or transparent. In particular instances, the electronic device can be a photovoltaic cell or can include a photovoltaic cell. Said cell may not include an electrolyte. The photovoltaic cell can be designed such that it is a single active layer, a bi-layer, or multiple-layer staking or bulk heterojunction layer photovoltaic cell. A bulk-heterojunction layer can be produced by using the compounds of the present invention alone or in combination with known small molecule, oligomers, or polymers, or combinations thereof. The photovoltaic cell can be included in an organic electronic device. Examples of such devices include organic light-emitting diodes (OLEDs) (e.g., polymeric organic light-emitting diodes (PLEDs), small-molecule organic light-emitting diodes (SM-OLEDs), organic integrated circuits (O-ICs), organic field effect transistors (OFETs), organic thin film transistors (OTFTs), organic solar cell (O-SCs), and organic laser diodes (O-lasers).

Also disclosed is a process for applying an organic or hybrid semiconducting or conducting layer on a substrate or an electrode, wherein the semiconducting or conducting layer comprises any one of the compounds of the present invention. The process can include disposing said semiconducting or conducting layer on said substrate or said electrode. The semiconducting layer can be photoactive. The conducting layer can be photoactive. The substrate can be rigid or flexible. The substrate can include an electrode and the photoactive layer can be disposed on said electrode. The substrate may not include an electrode, and the photoactive layer can be disposed on the substrate. The substrate can include an electrode and the photoactive layer can be disposed on the substrate or the electrode or onto both. Deposition of said layer can be by spray coating, ultra sonic spray coating, roll-to-roll coating, drop casting, dip coating, Mayer rod coating, gravure coating, slot die coating, doctor blade coating, spin coating, meniscus coating, transfer printing, ink-jet printing, offset printing or screen printing process. Alternatively, deposition of said layer can be by vacuum deposition or organic vapor phase deposition (OVPD), solution precipitation, organic molecular beam deposition, or vacuum thermal evaporation (VTE). In preferred aspects, vacuum deposition is vacuum thermal deposition.

A linear aliphatic group is a substituted or unsubstituted, saturated hydrocarbon with no tertiary or quaternary carbons. Aliphatic group substituents include, but are not limited to halogen, hydroxyl, alkyoxy, haloalkyl, haloalkoxy, carboxylic acid, ester, amine, amide, nitrile, acyl, thiol and thioether.

A branched aliphatic group is a substituted or unsubstituted, saturated hydrocarbon that includes at least one tertiary and/or quaternary carbon. Branched aliphatic group substituents include, but are not limited to alkyl, halogen, hydroxyl, alkyoxy, haloalkyl, haloalkoxy, carboxylic acid, ester, amine, amide, nitrile, acyl, thiol and thioether.

A cyclic aliphatic group is a substituted or unsubstituted, saturated, hydrocarbon that includes at least one ring in its structure. Polycyclic aliphatic groups may include fused, e.g., decalin, and/or spiro, e.g., spiro[5.5]undecane, polycyclic groups. Cyclic aliphatic group substituents include, but are not limited to alkyl, halogen, hydroxyl, alkyoxy, haloalkyl, haloalkoxy, carboxylic acid, ester, amine, amide, nitrile, acyl, thiol and thioether.

An aryl group is a substituted or unsubstituted, mono- or polycyclic hydrocarbon with alternating single and double bonds within each ring structure. Aryl group substituents include, but are not limited to alkyl, halogen, hydroxyl, alkyoxy, haloalkyl, haloalkoxy, carboxylic acid, ester, amine, amide, nitrile, acyl, thiol and thioether.

A heteroaryl group is a mono- or polycyclic hydrocarbon with alternating single and double bonds within each ring structure, and at least one atom within at least one ring is not carbon. Heteroaryl group substituents include, but are not limited to alkyl, halogen, hydroxyl, alkyoxy, haloalkyl, haloalkoxy, carboxylic acid, ester, amine, amide, nitrile, acyl, thiol and thioether.

An aromatic group is a substituted or unsubstituted, mono- or polycyclic hydrocarbon with alternating single and double bonds within each ring structure. Aromatic group substituents include, but are not limited to alkyl, halogen, hydroxyl, alkyoxy, haloalkyl, haloalkoxy, carboxylic acid, ester, amine, amide, nitrile, acyl, thiol and thioether.

A hetero-aromatic group is a mono- or polycyclic hydrocarbon with alternating single and double bonds within each ring structure, and at least one atom within at least one ring is not carbon. Hetero-aromatic group substituents include, but are not limited to alkyl, halogen, hydroxyl, alkyoxy, haloalkyl, haloalkoxy, carboxylic acid, ester, amine, amide, nitrile, acyl, thiol and thioether.

An alkyl group is linear or branched, substituted or unsubstituted, saturated hydrocarbon. Alkyl group substituents may include, but are not limited to alkyl, halogen, hydroxyl, alkyoxy, haloalkyl, haloalkoxy, carboxylic acid, ester, amine, amide, nitrile, acyl, thiol and thioether.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compounds and related processes of making and using said compounds, the photoactive layers, the photovoltaic cells, and the organic electronic devices of the present invention can "comprise," "consist essentially of," or "consist of" particular ingredients, components, compounds, compositions, etc. disclosed throughout the specification. With respect to the transitional phase "consisting essentially of," in one non-limiting aspect, a basic and novel characteristic of the aforesaid compounds are their light absorption and charge carrier mobility properties.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1:
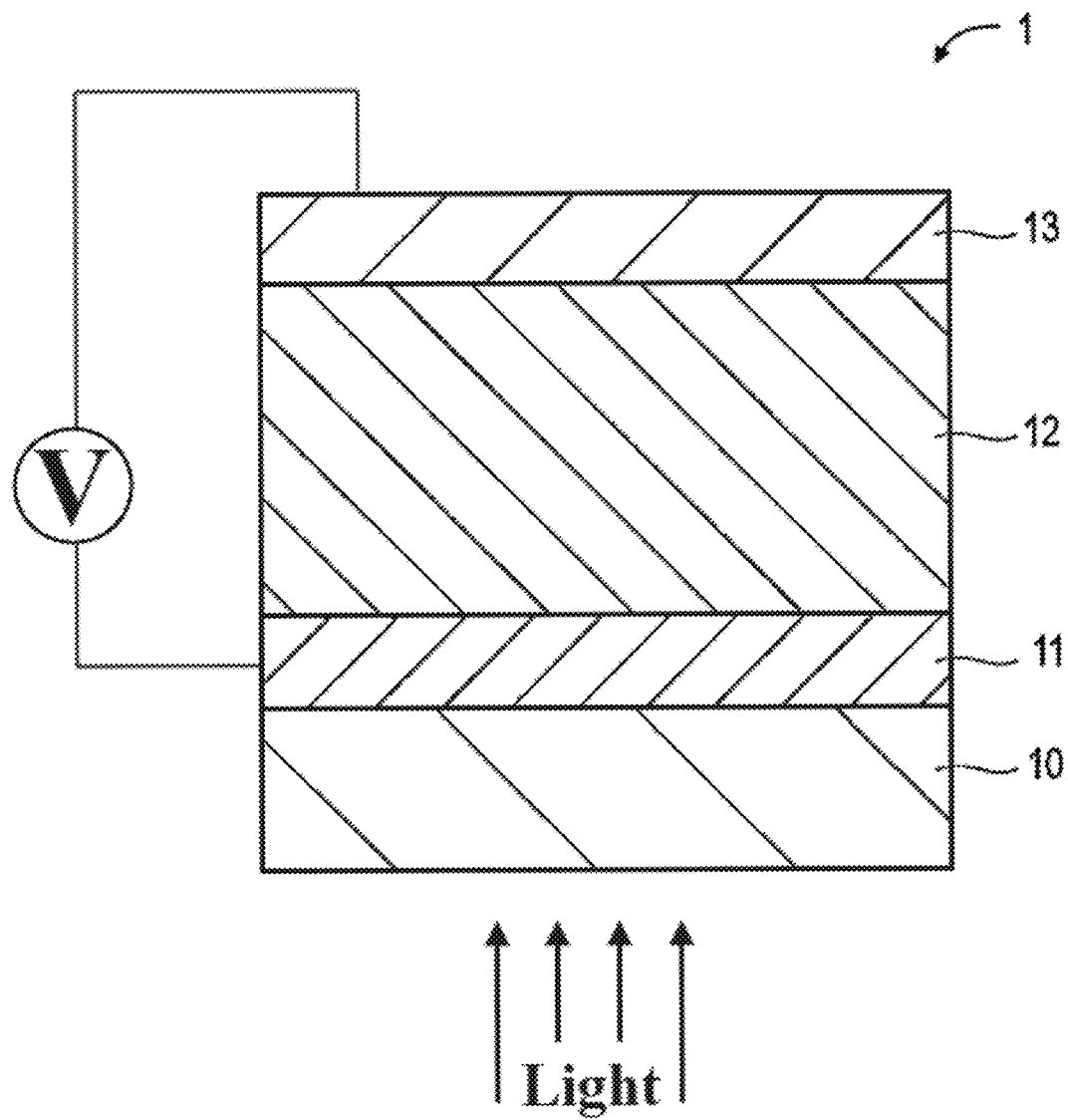
FIG. 1: Illustration of an organic photovoltaic cell incorporating the small molecules or oligomers or polymers or all types of the present invention.

As explained above, the present invention offers a solution to the problems associated with current small molecules and oligomers that are used in organic electronic devices. The solution resides in the creation of small molecules or oligomers or polymers that have low band gap semiconducting properties due to the presence of a delocalized pi-electron system that has alternating electron rich (donor) and electron-deficient (acceptor) units. Heavy group 16 elements such as selenium and tellurium are used at the core of acceptor units, thereby allowing for improved light absorption properties and enhanced electronic properties, including increased charge carrier mobility.

These and other non-limiting aspects of the present invention are discussed in detail in the following sections.

A. Semi-Conductive or Conductive Compounds

The compounds of the present invention can be prepared as small molecules or small oligomers or polymers that contain a central electron rich monomeric unit (or electron donor unit) or units in instances where oligomers are concerned that have at least two electron rich monomeric units that are connected to at least one or two comparatively electron deficient monomeric unit or units (or electron acceptor units) that feature heavy group 16 heteroatoms selenium or tellurium or combinations thereof. The compounds, oligomers, or polymers can be semi-conductive or conductive. The electron rich monomeric unit can be linked together with up to five such units. Similarly, the electron deficient monomeric unit can be linked together with up to five such units. Larger units are also contemplated and can be prepared to achieve a desired compound or oligomer. Further each small molecule or oligomer can be terminated with a thiophene capping unit. In addition to the compounds prepared in the Examples, the following provides non-limiting schemes that can be used to prepare small molecules and oligomers of the present invention. Notably, the small molecules and oligomers and polymers can be modified with additional non-functional or functional groups as desired. Further the small molecules and oligomers and polymers are soluble in common organic solvents, examples of which are provided below, and are stable for extended periods of time under ambient conditions.

The following reaction scheme 1 illustrates a non-limiting process to make monomeric electron acceptor units that can be used with the small molecules and oligomers of the present invention:

Scheme 1

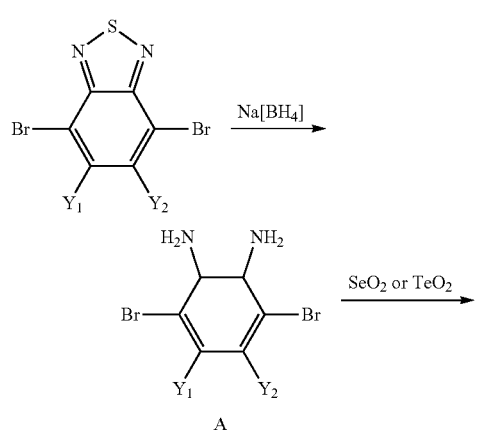

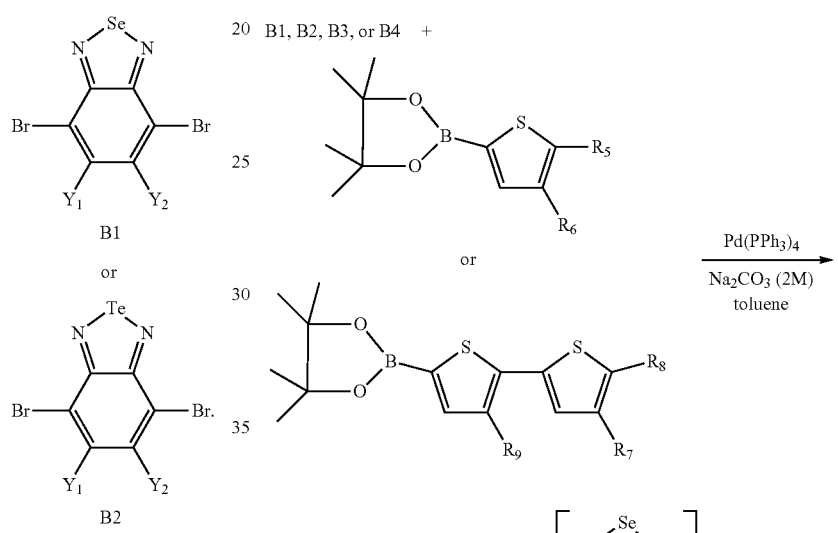

Referring to Scheme 1, excess (5-10) of equivalent Na[BH$_4$] can be used to synthesize compound A. Also, each of compounds B1 and B2 can be linked together to create small oligomers. In preferred aspects, the oligomers contain up to 5 monomeric units (i.e., n can be an integer of 1, 2, 3, 4, or 5). More monomeric units can be added if desired. This oligomerization step can be performed by using well established coupling reactions such as Suzuki coupling where compounds B1 and/or B2 are coupled with a boronic acid or boronic ester containing moiety. The desired coupling reaction can also be carried out using Stille coupling when compounds B1 and/or B2 are reacted with a tin containing organic moiety to produce compounds B3 and B4:

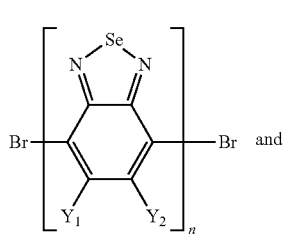

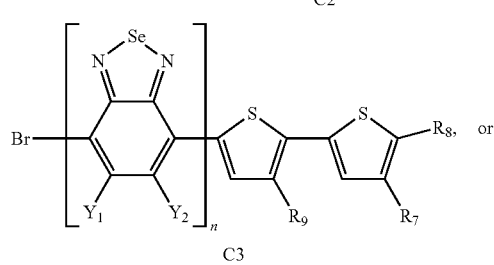

The produced B1, B2, B3, and B4 compounds can then be used in reaction scheme 2 to obtain thiophene end units or caps:

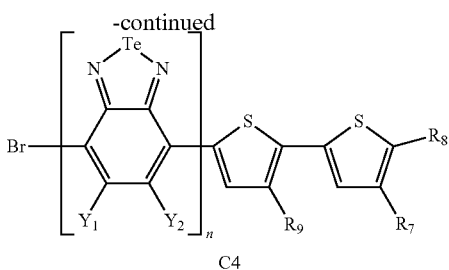

Referring to scheme 2, the reaction can be performed under Suzuki coupling reaction conditions and the catalyst Pd(PPh$_3$)$_4$, solvent (toluene) and activator (Na$_2$CO$_3$) can vary depending on the reaction. In some cases, different sets of catalysts, solvents and activators can be used. Also the percentage of product formation can change by modifying these parameters. Alternatively, the small molecule or oligomer can be terminated with an aromatic, hetero-aromatic, or alkyl functional group rather than with a thiophene capping unit. The $R_5$, $R_6$, $R_7$, $R_8$, $R_9$, and $Y_1$ and $Y_2$ groups are defined above in the summary of the invention section and in the claims, the definitions of which are incorporated into this section by reference. The C1, C2, C3, and C4 compounds can then be covalently linked to an electron donor unit.

Scheme 3 provides a non-limiting process to make electron donor units of the present invention:

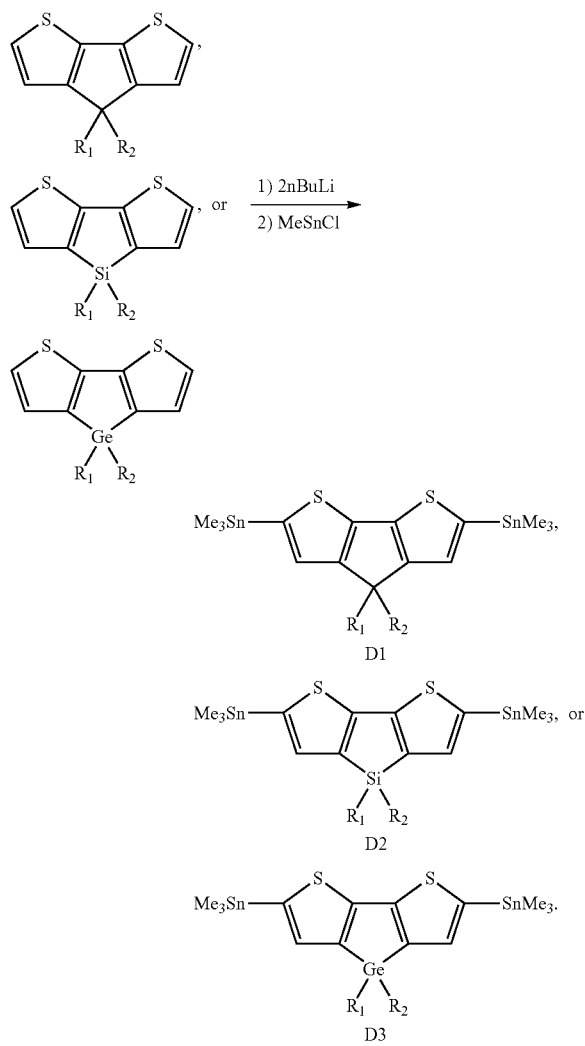

Referring to scheme 3, 2nBuLi and MeSnCl can be used in excess than the stoichiometric amount to synthesize compounds D1, D2, and D3. The $R_1$ and $R_2$ groups are defined above in the summary of the invention section and in the claims, the definitions of which are incorporated into this section by reference. Also, each of D1, D2, and D3 can be linked together to create small oligomers. In preferred aspects, the oligomers contain up to 5 monomeric units (i.e., m can be an integer of 1, 2, 3, 4, or 5). More monomeric units can be added if desired. This oligomerization step can be performed by using Stille coupling reaction where compounds D1, D2 and D3 can be reacted with any halide (R—Cl, R—Br and R—I) containing organic moiety to produce compounds D4, D5, and D6:

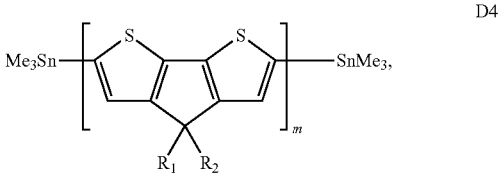

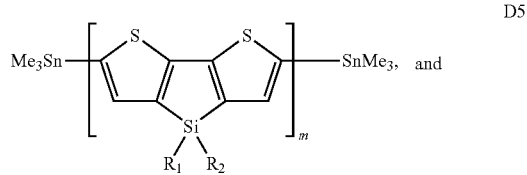

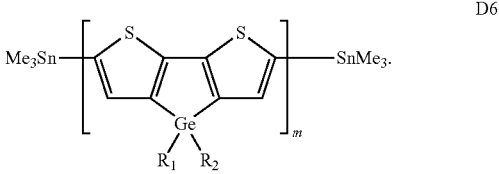

Each of the produced electron acceptor and donor units can then be covalently linked together to form a variety of various compounds (i.e., small molecules and oligomers) of the present invention. The covalent link between the acceptor and donor units can be made by reacting the bromine group on the electron donor unit with the trimethyltin group(s) present on the electron donor unit by using the following reaction conditions. A microwave glass tube can be charged with reagent C (C1, or C2, or C3, or C4), D (D1, or D2, or D3, or D4, or D5, or D6), Pd(PPh$_3$)$_4$ and solvent (toluene). The glass tube can be sealed with a Teflon® cap and stirred at room temperature to form covalent link between the electron donor (D) and acceptor (C). The following includes non-limiting compounds of the present invention that can be made by utilizing the aforesaid reaction schemes, in which the R, M, Y, E, n, and m, groups and integers are those that have been previously defined in the summary of the invention section and claims of the specification.

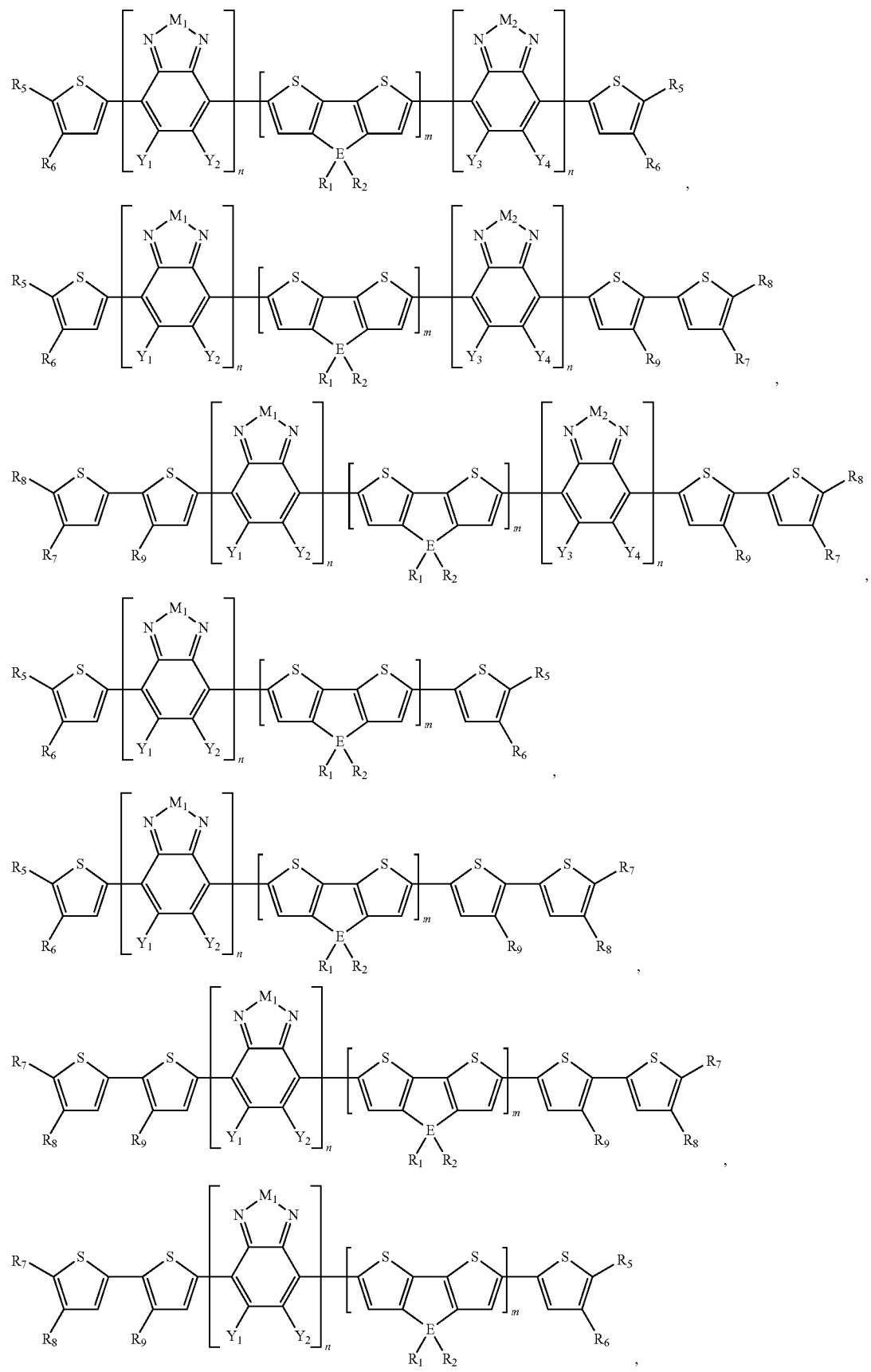

-continued

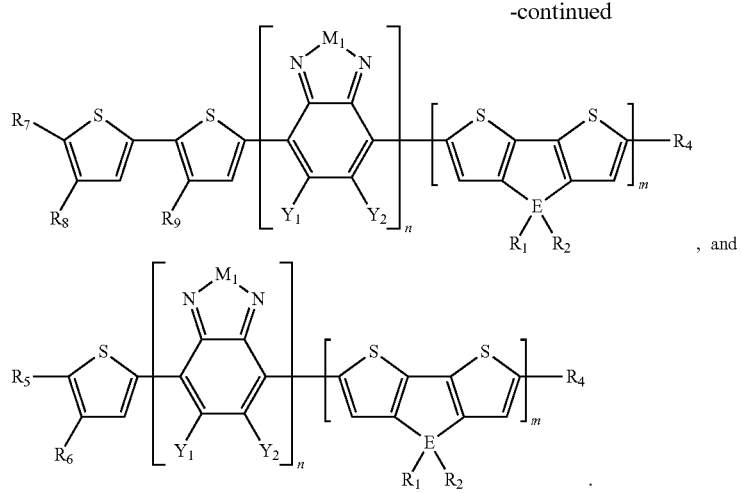

, and

Additionally, coordination complexes can be formed between the selenium and tellurium atoms (i.e., $M_1$ and $M_2$ groups)) on the compounds of the present invention with a coordination ligand, such as Cl, Br, I, a linear, branched or cyclic aliphatic, aryl or heteroaryl group of up to 20 carbon atoms. The formation of these coordination complexes can be used to increase the charge carrier mobility of the compounds of the present invention and further enhance their tenability for use in electronic devices.

B. Organic Photovoltaic Cells

The small molecules and oligomers of the present invention can be used in photovoltaic applications, such as organic photovoltaic cells. FIG. 1 is a cross-sectional view of a non-limiting organic photovoltaic cell of the present invention, in which the photoactive layer is formed with the small molecules or oligomers of the present invention, or combinations thereof. Notably, polymers do not have to be used to form said photoactive layer. However, and if desired, polymers can be used in combination with the disclosed small molecules or oligomers. The organic photovoltaic cell (1) can include a transparent substrate (10), a front electrode (11), a photoactive layer (12), and a back electrode (13). Additional materials, layers, and coatings (not shown) known to those of ordinary skill in the art can be used with photovoltaic cell (1), some of which are described below.

Generally speaking, the organic photovoltaic cell (1) can convert light into usable energy by: (a) photon absorption to produce excitons; (b) exciton diffusion; (c) charge transfer; and (d) charge separation and transportation to the electrodes. With respect to (a), the excitons are produced by photon absorption by the photoactive layer (12), which can be a single layer such that the compounds of the present invention are the active light absorbing component in the layer. In preferred aspects, and given that the compounds of the present invention have both electron donor and acceptor regions, the preferred layer (12) is a bulk heterojunction single layer. However, multiple layers are also contemplated in the context of the present invention (e.g., a bi-layer, tri-layer, or multiple-layer staking or bulk heterojunction layers). For (b), the generated excitons diffuse to the p-n junction. Then in (c), the charge is transferred to the other constituent of the BHJ. For (d), electrons and holes are separated and transported to the electrodes (11) and (13) and are used in a circuit.

1. Substrate (10)

The substrate (10) can be used as support. For organic photovoltaic cells, it is typically transparent or translucent, which allows light to efficiently enter the cell. It is typically made from material that is not easily altered or degraded by heat or organic solvents, and as already noted, has excellent optical transparency. Non-limiting examples of such materials include inorganic materials such as alkali-free glass and quartz glass, polymers such as polyethylene, PET, PEN, polyimide, polyamide, polyamidoimide, liquid crystal polymer, and cycloolefin polymer, silicon, and metal.

2. Front Electrode and Back Electrodes (11) and (13)

The front electrode (11) can be used as a cathode or anode depending on the set-up of the circuit. It is stacked on the substrate (10). The front electrode (11) can be made of a transparent or translucent conductive material. Alternatively, the front electrode (11) can be made of opaque or reflective material. Typically, the front electrode (11) is obtained by forming a film using such a material (e.g., vacuum deposition, sputtering, ion-plating, plating, coating, etc.). Non-limiting examples of transparent or translucent conductive material include metal oxide films, metal films, and conductive polymers. Non-limiting examples of metal oxides that can be used to form a film include indium oxide, zinc oxide, tin oxide, and their complexes such as indium stannate (ITO), fluorine-doped tin oxide (FTO), and indium zinc oxide films. Non-limiting examples of metals that can be used to form a film include gold, platinum, silver, and copper. Non-limiting examples of conductive polymers include polyaniline and polythiophene. The thickness of the film for the front electrode (11) is typically between from 30 to 300 nm. If the film thickness is less than 30 nm, then the conductivity can be reduced and the resistance increased, which results in a decrease in photoelectric conversion efficiency. If the film thickness is greater than 300 nm, then light transmittance may be lowered. Also, the sheet resistance of the front electrode (11) is typically 10Ω/□ or less. Further, the front electrode (11) may be a single layer or laminated layers formed of materials each having a different work function.

The back electrode (13) can be used as a cathode or anode depending on the set-up of the circuit. This electrode (13) can be made of a transparent or translucent conductive material. Alternatively, it (13) can be made of opaque or reflective material. This electrode (13) can be stacked on the photoactive layer (12). The material used for the back electrode (13) can be conductive. Non-limiting examples of such materials include metals, metal oxides, and conductive polymers (e.g., polyaniline, polythiophene, etc.) such as those discussed above in the context of the front electrode (11). When the front electrode (11) is formed using a material having high work function, then the back electrode (13) can be made of material having a low work function. Non-limiting examples of materials having a low work function include Li, In, Al, Ca, Mg, Sm, Tb, Yb, Zr, Na, K, Rb, Cs, Ba, and the alloys thereof. The back electrode (13) can be a single layer or laminated layers formed of materials each having a different work function. Further, it may be an alloy of one or more of the materials having a low work function and at least one selected from the group consisting of gold, silver, platinum, copper, manganese, titanium, cobalt, nickel, tungsten, and tin. Examples of the alloy include a lithium-aluminum alloy, a lithium-magnesium alloy, a lithium-indium alloy, a magnesium-silver alloy, a magnesium-indium alloy, a magnesium-aluminum alloy, an indium-silver alloy, and a calcium-aluminum alloy. The film thickness of the back electrode (13) can be from 1 to 1000 nm or from 10 to 500 nm. If the film thickness is too small, then the resistance can be excessively large and the generated charge may not be sufficiently transmitted to the external circuit.

In some embodiments, the front (11) and back (13) electrodes can be further coated with hole transport or electron transport layers (not shown in FIG. 1) to increase the efficiency and prevent short circuits of the organic photovoltaic cell (1). The hole transport layer and the electron transport layer can be interposed between the electrode and the photoactive layer (12). Non-limiting examples of the materials that can be used for the hole transport layer include polythiophene-based polymers such as PEDOT/PSS (poly(3,4-ethylenedioxythiophene)-poly(styrene sulfonate)) and organic conductive polymers such as polyaniline and polypyrrole. The film thickness of the hole transport layer can be from 20 to 100 nm. If the film thickness is too thin, short circuit of the electrode can occur more readily. If the film thickness is too thick, the film resistance is large and the generated electric current could be limited and optical conversion efficiency can be reduced. As for the electron transport layer, it can function by blocking holes and transporting electrons more efficiently. Non-limiting examples of the type of material that the electron transport layer can be made of include metal oxides (e.g., amorphous titanium oxide). When titanium oxide is used, the film thickness can range from 5 to 20 nm. If the film thickness is too thin, the hole blocking effect can be reduced and thus the generated excitons are deactivated before the excitons dissociate into electrons and holes. By comparison, when the film thickness is too thick, the film resistance is large, the generated electric current is limited, resulting in reduction of optical conversion efficiency.

3. Photoactive Layer (12)

The photoactive layer (12) can be an organic or hybrid semiconducting or conducting layer. The layer (12) can be interposed between the front electrode (10) and the back electrode (13). In one preferred instance, the photoactive layer (12) can be a bulk hetero-junction single layer such that the compounds of the present invention are the active light absorbing component in the layer. The layer (12) can absorb light and allow for the flow of electrons to and from the electrodes (11 and 13). Further, there can be multiple photoactive layers used for a given photovoltaic cell (e.g., 2, 3, 4, or more).

Given the unique properties of the compounds (i.e., small molecules and oligomers) of the present invention, many options are available for forming the photoactive photoactive layer (12) on at least a portion of a surface of the electrodes (11 and 13) or on the substrate (10) or both. By way of example, vacuum thermal evaporation, which involves the heating of an organic material in vacuum and depositing said material, or organic vapor phase deposition, which involves evaporation of the organic material over a substrate in the presence of an inert carrier gas, can be used. However, the increased solubility of the compounds of the present invention also allows for the formation of a solution that can then be deposited onto said surfaces. In particular, the compounds of the present invention can be fully or partially solubilized within a solution and then deposited onto a given surface via solution-based deposition techniques (e.g., spray coating, role-to-role coating, drop casting, dip coating, Mayer rod coating, doctor blade coating, spin coating, meniscus coating, transfer printing, ink jet printing, offset printing, screen printing, gravure printing, flexo printing, dispenser coating, nozzle coating, capillary coating, etc.). Non-limiting examples of solvents that can be used in the context of the present invention include unsaturated hydrocarbon-based solvents (such as toluene, xylene, tetralin, decalin, mesitylene, n-butylbenzene, sec-butylbutylbenzene, and tert-butylbenzene), halogenated aromatic hydrocarbon-based solvents (such as chlorobenzene, dichlorobenzene, and trichlorobenzene), halogenated saturated hydrocarbon-based solvents (such as carbon tetrachloride, chloroform, dichloromethane, dichloroethane, chlorobutane, bromobutane, chloropentane, chlorohexane, bromohexane, and chlorocyclohexane), ethers (such as tetrahydrofuran and tetrahydropyran), and polar aprotic solvents (such as dichloromethane (DCM), tetrahydrofuran (THF), ethyl acetate, propyl acetate, butyl acetate, isobutylacetate (and the like), acetone, dimethylformamide (DMF), acetonitrile (MeCN), benzonitrile, nitromethane, dimethyl sulfoxide (DMSO), propylene carbonate, or N-methyl-2-pyrrolidone (NMP), sulfolane (tetramethylene sulfone, 2,3,4,5-tetrahydrothiophene-1,1-dioxide), hexamethylphosphoramide (HMPA), methyl ethyl ketone, methyl isobutyl ketone, acetophenone, benzophenone, or the like), or any combination of said solvents.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

(Synthesis of 7,7'-(4,4-Bis(2-ethylhexyl)-4H-silolo[3,2-b:4,5-b']dithiophene-2,6-diyl)bis(6-fluoro-4-(5'-hexyl-[2,2'-bithiophen]-5-yl)benzo[c][1,2,5]seleno-diazole) (p-DTS(FBTSe$_2$)$_2$))

Synthesis of 1,2-Diamino-3,6-dibromo-4-fluorobenzene (A): 4,7-Dibromo-5-Fluorobenzo[c][1,2,5]thiadiazole (2.00 g, 6.41 mmol) and ethanol (50 mL) were added to a three-necked round-bottom flask and cooled to 0° C. After addition of Na[BH$_4$] (4.6 g, 0.12 mol) was slowly added, the reaction mixture was stirred overnight at room temperature. After removal of the volatiles 100 distilled water was added to the reaction mixture and then the mixture was extracted with ether, washed with brine, dried over anhydrous Na$_2$SO$_4$. Volatiles were removed from the extract to obtain A as a pale brown powder (1.20 g, 66%). $^1$H NMR (300 MHz, CDCl$_3$): δ 6.80 (d, 1H, $^3J_{HF}$=7.8 Hz, ArH), 4.14 (s, 1H, NH), 3.62 (s, 1H, NH). $^{13}$C{$^1$H} (500 MHz, CDCl$_3$): δ 95.7 (d, $^3J_{CF}$=24.1 Hz, ArC), 108.7 (d, $^3J_{CF}$=26.3 Hz, ArC), 109.4 (d, $^4J_{CF}$=11.3 Hz, ArC), 128.8 (ArC), 135.8 (ArC), 153.2 (d, $^1J_{CF}$=240.2 Hz, ArC). $^{19}$F NMR (376 MHz, CDCl$_3$): δ −116.1 (d, $^3J_{HF}$=8.3 Hz). FIRMS (EI) m/z calc. for C$_6$H$_5$N$_2$$^{79}$Br$^{81}$BrF (283.87830). Found 283.8784.

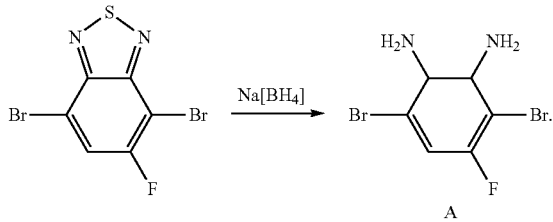

Synthesis of 4,7-Dibromo-5-Fluorobenzo[c][1,2,5]seleno-diazole (B)

A solution of compound A (1.02 g, 3.61 mmol) in 30 mL of ethanol was heated to reflux in a three-necked round-bottom flask with stirring. Afterwards, a solution of SeO$_2$ (0.402 g, 3.62 mmol) in 20 mL of hot water was added dropwise. The resulting reaction mixture was refluxed for overnight to obtain a yellow precipitate over pale brown solution. Then, the reaction was cooled to room temperature and precipitate was filtrated, and washed with 5×100 mL of ethanol to obtain B as a golden-yellow powder (1.1 g, 85%). $^1$H NMR (300 MHz, CDCl$_3$): δ 7.75 (d, 1H, $^3J_{HF}$=6.8 Hz, ArH). $^{19}$F NMR (376 MHz, CDCl$_3$): δ −102.1 (d, $^3J_{HF}$=6.8 Hz). HRMS (EI) m/z calc. for C$_6$HN$_2$$^{79}$Br$^{81}$BrF$^{80}$Se (359.76352). Found 359.7637.

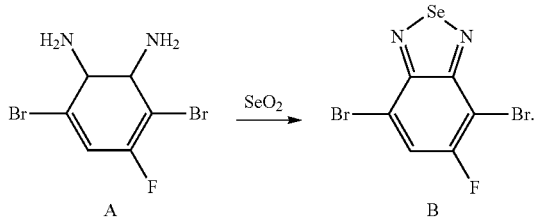

Synthesis of 4-Bromo-5-fluoro-7-(5'-hexyl-[2,2'-bithiophene]-5-yl)benzo[c][1,2,5]seleno-diazole (C)

A mixture of 30 mL of toluene and 20 mL aqueous solution of Na$_2$CO$_3$ (2.0 M) was degassed with nitrogen for 25 min. A Schlenk flask was charged with 4,7-Dibromobenzo[c][1,2,5]seleno-diazole (B) (1.48 g, 4.1 mmol) and 5'-hexyl-2,2'-bithiophene-5-boronic acid pinacol ester (1.6 g, 4.2 mmol), and Pd(PPh$_3$)$_4$ (0.15 g, 0.14 mmol) in a nitrogen atmosphere containing glove box. The solvent mixture was then transferred under nitrogen to the Schlenk containing reactants and the resulting mixture was then stirred and degassed for 25 min followed by the addition of 3 drop of Aliquat 336. The reaction mixture was heated to 85° C. overnight to obtain a bright red solution, quenched afterwards with water (15 mL). Organic layer was extracted with dichloromethane (50 mL), dried over Na$_2$SO$_4$ and then volatiles were removed under reduced pressure to give dark red solid. This crude product was loaded on a short silica column and eluted with hexanes to remove unreacted pinacol ester starting materials and Aliquat. After eluting the desired product with dichloromethane followed by removal of solvents yielded red solid which contained B as only remaining impurity. Spectroscopically pure C (0.738 g, 34%) was obtained by removing 7 from the product mixture by sublimation (70° C., 0.03 torr). $^1$H NMR (500 MHz, CDCl$_3$): δ 7.93 (d, $^3J_{HH}$=4.0 Hz, 1H, CH), 7.64 (d, $^3J_{HH}$=10.0 Hz, 1H, CH), 7.15 (d, $^3J_{HH}$=4.0 Hz, 1H, CH), 7.12 (d, $^3J_{HH}$=4.0 Hz, 1H, CH), 6.73 (d, $^3J_{HH}$=3.5 Hz, 1H, CH), 2.82 (t, $^3J_{HH}$=7.8 Hz, 2H, CH$_2$), 1.70 (m, J=7.5 Hz, 2H, CH$_2$), 1.40 (br m, 2H, CH$_2$), 1.34 (br m, 2H, CH$_2$), 1.30 (br m, 2H, CH$_2$), 0.99 (t, $^3J_{HH}$=7.2 Hz, 3H, CH$_3$). $^{19}$F NMR (376 MHz, CDCl$_3$): δ −103.1 (d, $^3J_{HF}$=10.0 Hz). FIRMS (EI) m/z calc. for C$_{20}$H$_{18}$N$_2$$^{81}$Br$^{81}$FS$_2$$^{80}$Se (529.92350). Found 529.92236.

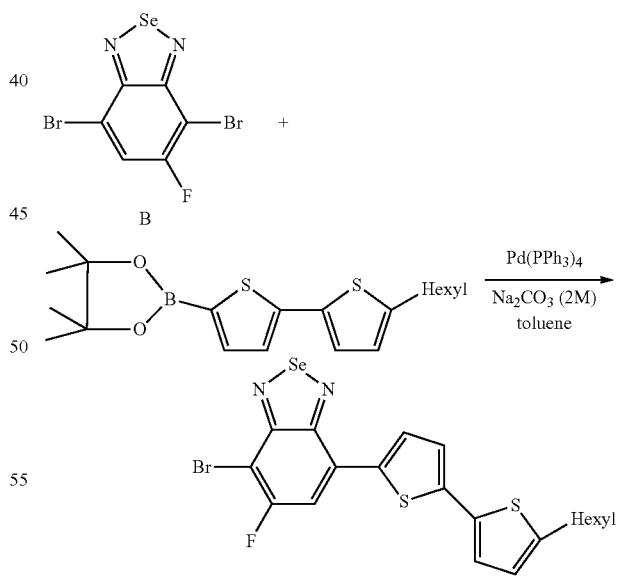

Synthesis of 5,5'-bis(trimethylstannyl)-3,3'-di-2-ethylhexylsilylene-2,2'-bithiophene (D)

To a solution of 3,3'-di-2-ethylhexylsilylene-2,2'-bithiophene (1.16 g, 2.78 mmol) in 50 mL of dry THF was added 3.8 mL (6.08 mmol, 1.6 M solution in hexanes) of nBuLi was in hexane at −78° C. The reaction mixture was allowed to warm to room temperature and stirred for 2 h leading to the formation of a thick suspension. The resulting suspension was then cooled to −78° C. and 6.92 mL of Me$_3$SnCl (6.92 mmol, 1.0 M solution in THF) was added dropwise. The reaction was warmed to room temperature and stirred overnight. The mixture was quenched with distilled water, poured into a separation funnel and organic layer was extracted with 150 mL of hexanes. The organic layer was separated, further washed with 5×100 mL of water and afterwards dried over Na$_2$SO$_4$. Removal of the volatiles under high vacuum for overnight afforded compound D as a dark brown oil (1.90 g, 92%). $^1$H NMR (400 MHz, CDCl$_3$): δ 7.07 (s, 2H, satellites: $^3J_{H\text{-}119/117Sn}$=24.4 Hz, ArH), 1.29-0.75 (m, 34H, CH), 0.37 (s, 18H, Sn(CH$_3$)$_3$, satellites: $^2J_{H\text{-}119Sn}$=57.6 Hz, $^2J_{H\text{-}117Sn}$=55.17 Hz).

Synthesis of 7,7'-(4,4-Bis(2-ethylhexyl)-4H-silolo[3,2-b:4,5-b']dithiophene-2,6-diyl)bis(6-fluoro-4-(5'-hexyl-[2,2'-bithiophen]-5-yl)benzo[c][1,2,5]selenodiazole) (p-DTS(FBTSe$_2$)$_2$) (1)

A 20 mL microwave glass tube was charged with C (350 mg, 0.66 mmol), D (246 mg, 0.32 mmol), Pd(PPh$_3$)$_4$ (30 mg, 0.024 mmol) and 15 of dry toluene. The glass tube was sealed with a Teflon® cap and stirred at room temperature for 15 minutes. Afterwards, the reaction mixture was heated to 100° C. for 1 minute, 125° C. for 1 minute, 140° C. for 10 minutes, 150° C. for 10 minutes, and 160° C. for 10 minutes in a Biotage microwave reactor. After cooling the reaction mixture to room temperature, the crude product mixture was then loaded onto a short silica gel bed, washed with methanol (most of the impurities are soluble in methanol but not the desired product) and then eluted using CH$_2$Cl$_2$. After collecting the CH$_2$Cl$_2$ soluble fraction volatiles were removed under vacuum to obtain a green solid. The resulting solid was slurried in a mixture of methanol and hexanes (3:1), sonicated for 1 hour and stirred overnight at room temperature. The mother liquor was then decanted off and the precipitate was dried in vacuo. Spectroscopically pure 1 was isolated as a dark green solid (256 mg, 59%). $^1$H NMR (500 MHz, CDCl$_3$): δ 8.20 (t, 2H, CH), 7.91 (d, $^3J_{HH}$=4.0 Hz, 2H, CH), 7.68 (d, $^3J_{HH}$=13.0 Hz, 2H, CH), 7.15 (d, $^3J_{HH}$=4.0 Hz, 2H, CH), 7.10 (d, $^3J_{HH}$=4.0 Hz, 2H, CH), 6.71 (d, $^3J_{HH}$=4.0 Hz, 2H, CH), 2.81 (t, $^3J_{HH}$=7.5 Hz, 4H, CH$_2$), 1.70 (m, 4H, CH$_2$), 1.55 (m, 2H, CH$_2$), 1.40 (m, 4H, CH$_2$), 1.32 (m, 16H, CH$_2$), 1.22 (m, 8H, CH$_2$), 1.11 (m, 4H, CH$_2$), 0.92 (t, $^3J_{HH}$=7.2 Hz, 6H, CH$_3$), 0.83 (t, $^3J_{HH}$=7.2 Hz, 12H, CH$_3$). $^{19}$F NMR (376 MHz, CDCl$_3$): δ −108.1 (m). $^{29}$Si NMR (gHSQC, 400 MHz, CDCl$_3$): δ −4.8. $^{77}$Se NMR (76 MHz, CDCl$_3$) δ 1510.3. MALDI m/z calc. for C$_{64}$H$_{72}$F$_2$N$_4$S$_6$Se$_2$Si (1314.21561). Found 1314.21429. Anal. Calcd. for C$_{64}$H$_{72}$F$_2$N$_4$S$_6$Se$_2$Si: C, 58.50; H, 5.52; N, 4.26. Found: C, 58.28; H, 5.71; N, 4.24.

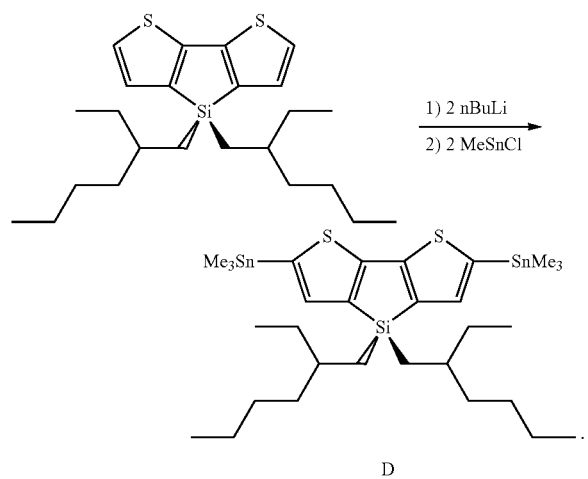

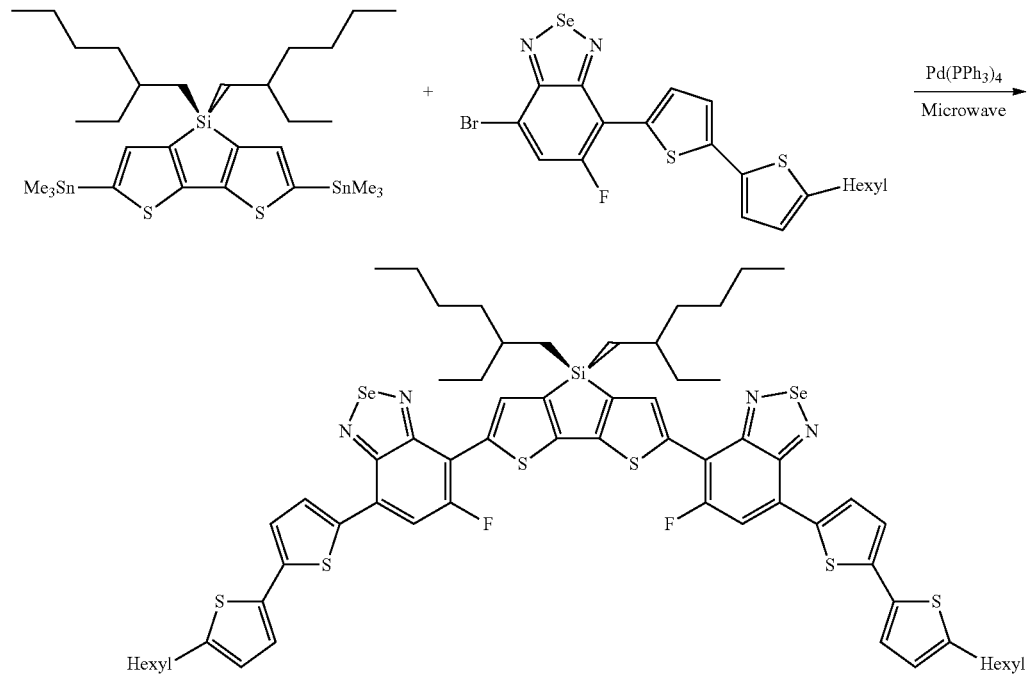

1

Figure 2:
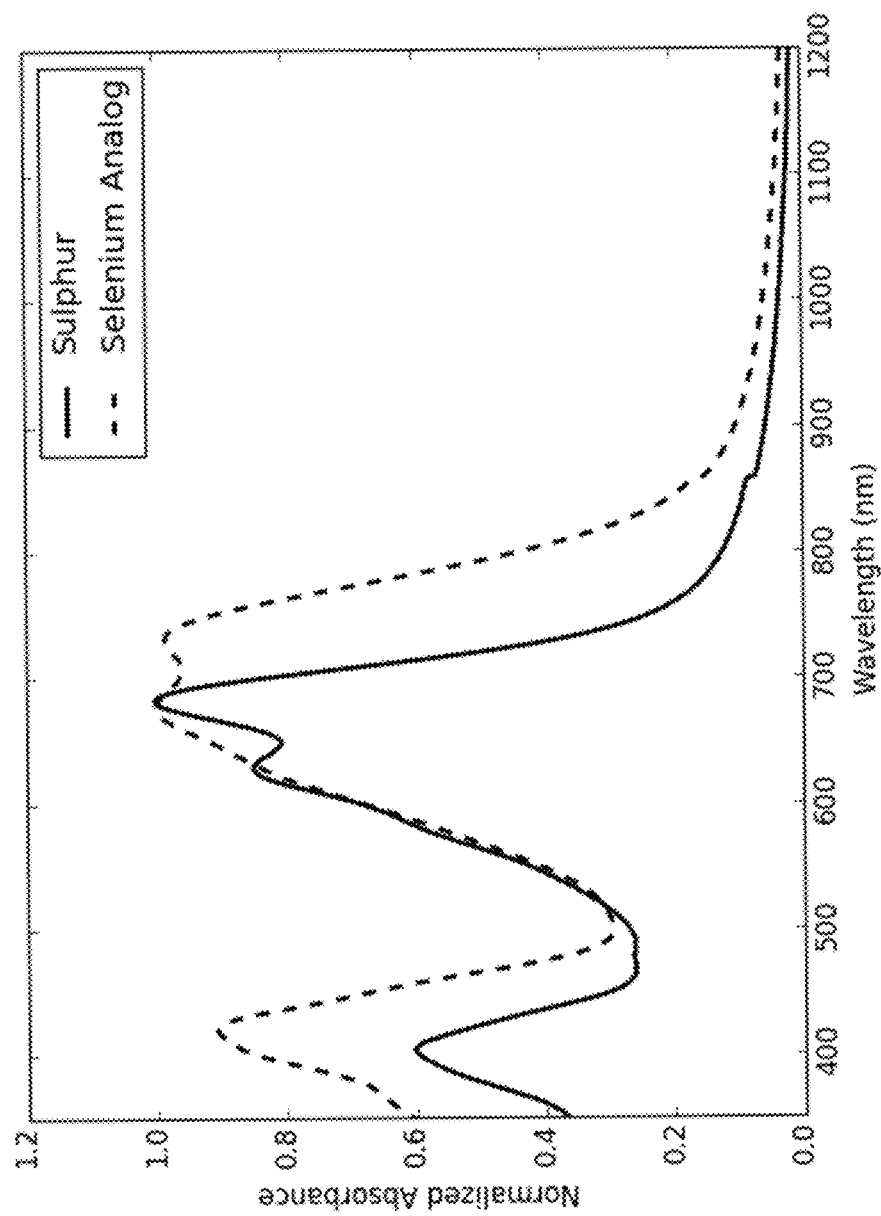
FIG. 2: Comparison of UV-visible absorption spectra of compound 1 (selenium) with sulfur analogue in a thin film form.

FIG. 2 provides data confirming the light absorbing properties of compound 1.

Example 2

(Synthesis of 7,7'-(4,4-Bis(2-ethylhexyl)-cyclopenta-[3,2-b:4,5-b']dithiophene-2,6-diyl)bis(6-fluoro-4-(5'-hexyl-[2,2'-bithiophen]-5-yl)benzo[c][1,2,5]seleno-diazole) (p-DTC(FBTSe₂)₂) (2))

Synthesis of 4,4'-Bis(2-ethylhexyl)-2,6-bis(trimethylstannyl)-4H-cyclopenta[2,1-b:3,4-b']dithiophene (E)

To a solution of 4,4'-Bis(2-ethylhexyl)-4H-cyclopenta[2,1-b:3,4-b']dithiophene (1.78 g, 4.42 mmol) in 50 mL of dry THF was added 6.10 mL (9.76 mmol, 1.6 M solution in hexanes) of nBuLi was in hexane at −78° C. The reaction mixture was allowed to warm to room temperature and stirred for 2 h leading to the formation of a thick yellow suspension. The resulting suspension was then cooled to −78° C. and 10.2 mL of trimethyltin chloride (10.2 mmol, 1.0 M solution in THF) was added dropwise over 20 min. The reaction was warmed to room temperature and stirred overnight. The resulting reaction mixture was quenched with distilled water, poured into a separation funnel and organic layer was extracted with 200 mL of hexanes. The organic layer was separated, further washed with 5×100 mL of water and afterwards dried over Na₂SO₄. Removal of the volatiles under high vacuum for overnight afforded compound E as a brown oil (1.72 g, 95%). ¹H NMR (300 MHz, CDCl₃): δ 6.94 (t, 2H, ArH), 1.84 (t, 4H, CH), 1.29 (m, 2H, CH), 0.99-0.87 (m, 18H, CH), 0.74 (t, 6H, CH), 0.58 (t, 8H, CH), 0.35 (s, 18H, Sn(CH₃)₃, satellites: ²$J_{H-119Sn}$=57.2 Hz, ²$J_{H-117Sn}$=54.9 Hz). ¹³C{¹H} (500 MHz, CDCl₃): δ −8.2 (Sn(CH₃)₃), 10.8 (CH), 14.2 (CH), 22.9(CH), 27.7 (CH), 28.8 (CH), 34.5 (CH), 35.2 (CH), 43.2 (CH), 52.2 (CH), 130.3 (ArC), 136.3 (ArC), 142.7 (ArC), 159.8 (ArC). HRMS (EI) m/z calc. for C₃₁H₅₄S₂¹¹⁶Sn (722.17017). Found 722.1789.

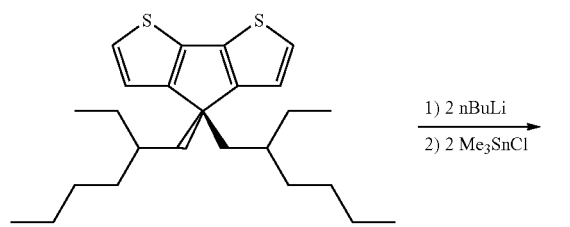

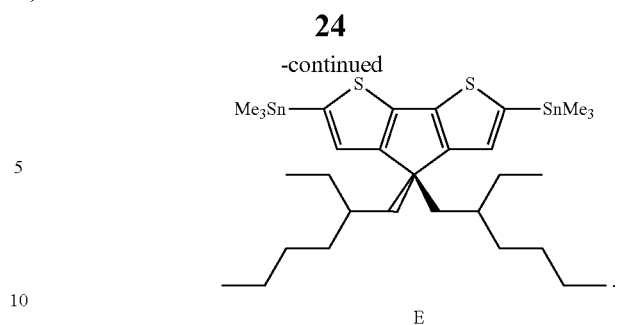

Synthesis of 7,7'-(4,4-Bis(2-ethylhexyl)-cyclopenta-[3,2-b:4,5-b']dithiophene-2,6-diyl)bis(6-fluoro-4-(5'-hexyl-[2,2'-bithiophen]-5-yl)benzo[c][1,2,5]seleno-diazole) (p-DTC(FBTSe₂)₂) (2)

A 20 mL microwave glass tube was charged with C (600 mg, 1.13 mmol), E (412 mg, 0.57 mmol), Pd(PPh₃)₄ (50 mg, 0.043 mmol) and 15 of dry toluene. The glass tube was sealed with a Teflon® cap and stirred at room temperature for 15 minutes. Afterwards, the reaction mixture was heated to 100° C. for 1 minute, 125° C. for 1 minute, 140° C. for 10 minutes, 150° C. for 10 minutes, and 160° C. for 10 minutes in a Biotage microwave reactor. After cooling the reaction mixture to room temperature, the crude product mixture was then loaded onto a short silica gel bed, washed with methanol (most of the impurities are soluble in methanol but not the desired product) and then eluted using CH₂Cl₂. After collecting the CH₂Cl₂ soluble fraction volatiles were removed under vacuum to obtain a green solid. The resulting solid was slurried in a mixture of methanol and hexanes (3:1), sonicated for 1 hour and stirred overnight at room temperature. The mother liquor was then decanted off and the precipitate was dried in vacuo. Spectroscopically pure 2 was isolated as a dark green solid (212 mg, 49%) after recrystallization from a CH₂Cl₂/pentane mixture. ¹H NMR (500 MHz, CDCl₃): δ 8.10 (t, 2H, CH), 7.94 (m, 2H, CH), 7.73 (d, ³$J_{HH}$=13.4 Hz, 2H, CH), 7.18 (d, ³$J_{HH}$=4.0 Hz, 2H, CH), 7.12 (d, ³$J_{HH}$=4.0 Hz, 2H, CH), 6.73 (d, ³$J_{HH}$=4.0 Hz, 2H, CH), 2.83 (t, ³$J_{HH}$=7.5 Hz, 4H, CH₂), 2.01 (m, 4H, CH₂), 1.71 (m, 4H, CH₂), 1.41 (m, 4H, CH₂), 1.33 (m, 8H, CH₂), 1.05 (m, 16H, CH₂), 0.92 (m, 6H, CH₂), 0.81 (t, ³$J_{HH}$=7.2 Hz, 6H, CH₃), 0.81 (m, 2H, CH₃), 0.66 (m, 12H, CH₃). ¹⁹F NMR (376 MHz, CDCl₃): δ −108.5 (m). MALDI m/z calc. for C₆₅H₇₂F₂N₄S₆Se₂ (1298.23860). Found 1298.23767.

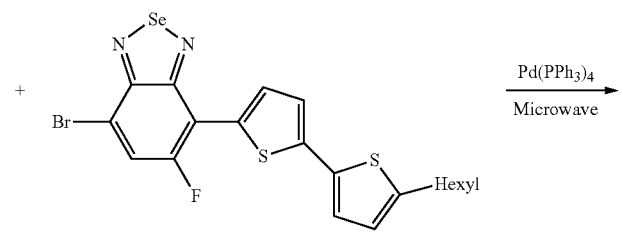

-continued

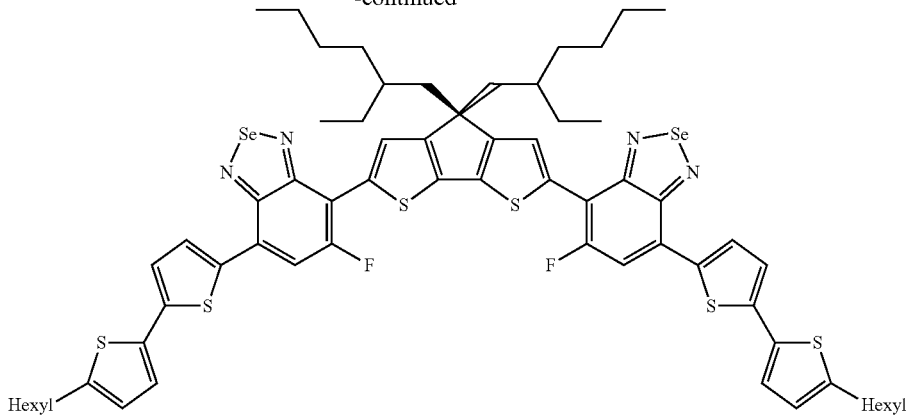

2

Figure 3:
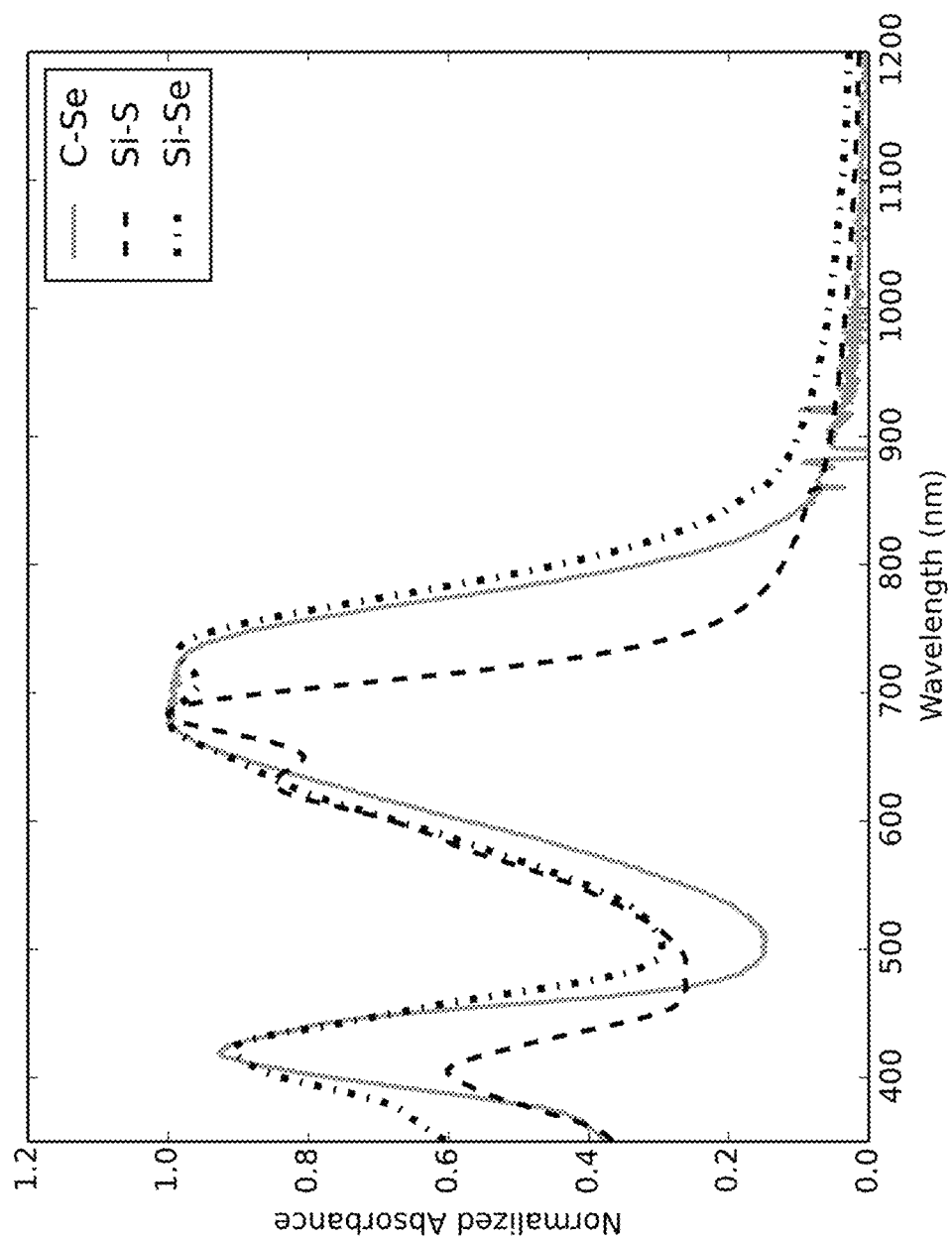
FIG. 3: UV-Visible absorption profile of small molecules 1 and 2 compared to their sulfur analogue.

FIG. 3 provides data confirming the light absorbing properties of compound 2 and comparing the absorption profiles of compounds 1 and 2 to their sulfur analogue.

The invention claimed is:

1. A compound having the following structure:

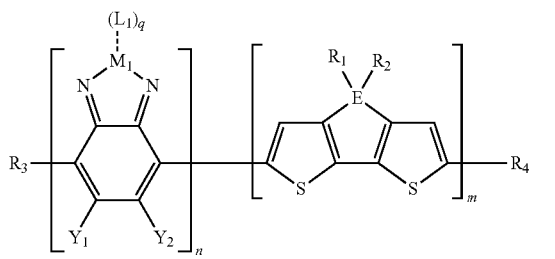

wherein:

E is C or Ge;

$R_1$ and $R_2$ are each independently a linear, branched or cyclic aliphatic, aryl or heteroaryl group of up to 20 carbon atoms;

$R_3$ is

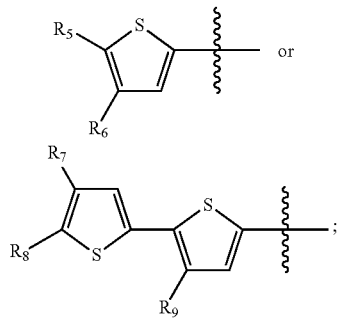

$R_4$ is

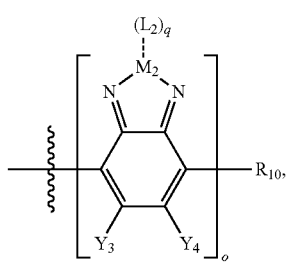

wherein $R_{10}$ is

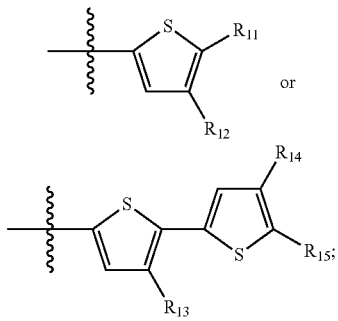

$R_5$, $R_6$, $R_7$, $R_8$, $R_9$, $R_{11}$, $R_{12}$, $R_{13}$, $R_{14}$, and $R_{15}$ are each independently H, a linear, branched or cyclic aliphatic, aryl or heteroaryl group of up to 20 carbon atoms, with the proviso that both of $R_5$ and $R_6$ are not H, both of $R_7$ and $R_8$ are not H, both of $R_{11}$ and $R_{12}$ are not H, and both of $R_{14}$ and $R_{15}$ are not H;

$M_1$ and $M_2$ are each individually Se or Te;

$L_1$ and $L_2$ are each individually a coordination ligand bound to $M_1$ and $M_2$, respectively, through a coordination bond, with q being an integer from 1 to 4; and $Y_1$, $Y_2$, $Y_3$, and $Y_4$ are each independently H, F, $NO_2$, CN, $N(R_{16})_2$, $OR_{17}$, $CF_3$, or $C_6H_zX_{6-z}$, or $Y_1$ and $Y_2$ or $Y_3$ and $Y_4$ are each N and are connected by a metal bridge atom to form, together with the carbon atoms to which they are attached, a 5 member ring system, wherein $R_{16}$ and $R_{17}$ are each independently a linear, branched or cyclic aliphatic, aryl or heteroaryl group of up to 20 carbon atoms, X is F, Cl or Br, and z is an integer from 0 to 6;

n and m are each integers from 1 to 5; and o is an integer from 0 to 5, with the proviso that when o is 0, then $R_4$ is either $R_3$ or an aromatic, heteroaromatic, or alkyl functional group.

2. The compound of claim 1, having the following structure:

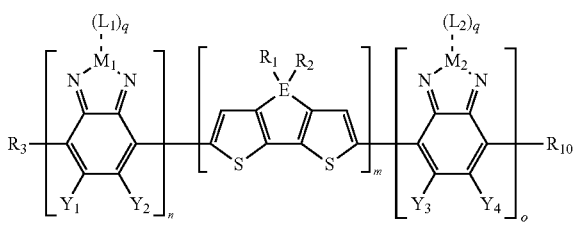

wherein:

E is C or Ge;

$R_1$ and $R_2$ are each independently a linear, branched or cyclic aliphatic, aryl or heteroaryl group of up to 20 carbon atoms;

$R_3$ is

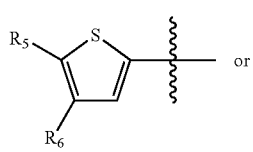

or

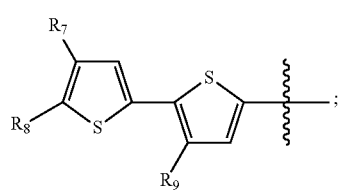

$R_{10}$ is

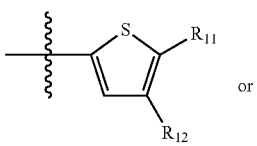

or

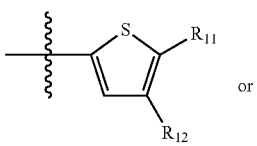

$R_5$, $R_6$, $R_7$, $R_8$, $R_9$, $R_{11}$, $R_{12}$, $R_{13}$, $R_{14}$, and $R_{15}$ are each independently H, a linear, branched or cyclic aliphatic, aryl or heteroaryl group of up to 20 carbon atoms, with the proviso that both of $R_5$ and $R_6$ are not H, both of $R_7$ and $R_8$ are not H, both of $R_{11}$ and $R_{12}$ are not H, and both of $R_{14}$ and $R_{15}$ are not H;

$M_1$ and $M_2$ are each individually Se or Te;

$L_1$ and $L_2$ are each individually a coordination ligand bound to $M_1$ and $M_2$, respectively, through a coordination bond, with q being an integer from 1 to 4; and $Y_1$, $Y_2$, $Y_3$, and $Y_4$ are each independently H, F, $NO_2$, CN, $N(R_{16})_2$, $OR_{17}$, $CF_3$, or $C_6H_zX_{6-z}$, or $Y_1$ and $Y_2$ or $Y_3$ and $Y_4$ are each N and are connected by a metal bridge atom to form, together with the carbon atoms to which they are attached, a 5 member ring system, wherein $R_{16}$ and $R_{17}$ are each independently a linear, branched or cyclic aliphatic, aryl or heteroaryl group of up to 20 carbon atoms, X is F, Cl or Br, and z is an integer from 0 to 6;

n and m are each integers from 1 to 5; and o is an integer from 0 to 5, with the proviso that when o is 0, then $R_4$ is either $R_3$ or an aromatic, heteroaromatic, or alkyl functional group.

3. The compound of claim 1, having the following structure:

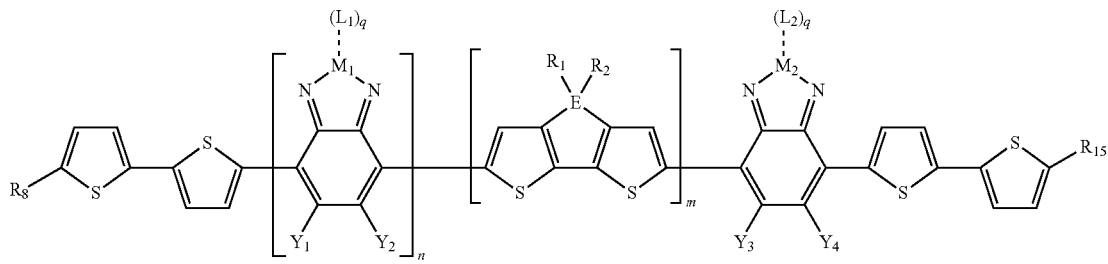

wherein:

E is C or Ge;

$R_1$ and $R_2$ are each independently a linear, branched or cyclic aliphatic, aryl or heteroaryl group of up to 20 carbon atoms;

$R_8$ and $R_{15}$ are each independently H, a linear, branched or cyclic aliphatic, aryl or heteroaryl group of up to 20 carbon atoms;

$M_1$ and $M_2$ are each individually Se or Te;

$L_1$ and $L_2$ are each individually a coordination ligand bound to $M_1$ and $M_2$, respectively, through a coordination bond, with q being an integer from 1 to 4; and $Y_1$, $Y_2$, $Y_3$, and $Y_4$ are each independently H, F, $NO_2$, CN, $N(R_{16})_2$, $OR_{17}$, $CF_3$, or $C_6H_zX_{6-z}$, or $Y_1$ and $Y_2$ or $Y_3$ and $Y_4$ are each N and are connected by a metal bridge atom to form, together with the carbon atoms to which they are attached, a 5 member ring system, wherein $R_{16}$ and $R_{17}$ are each independently a linear, branched or cyclic aliphatic, aryl or heteroaryl group of up to 20 carbon atoms, X is F, Cl or Br, and z is an integer from 0 to 6; and n and m are each integers from 1 to 5.

4. The compound of claim 1, wherein $L_1$ and $L_2$ are each individually Cl, Br, I, a linear, branched or cyclic aliphatic, aryl or heteroaryl group of up to 20 carbon atoms.

5. The compound of claim 1, having the following structure:

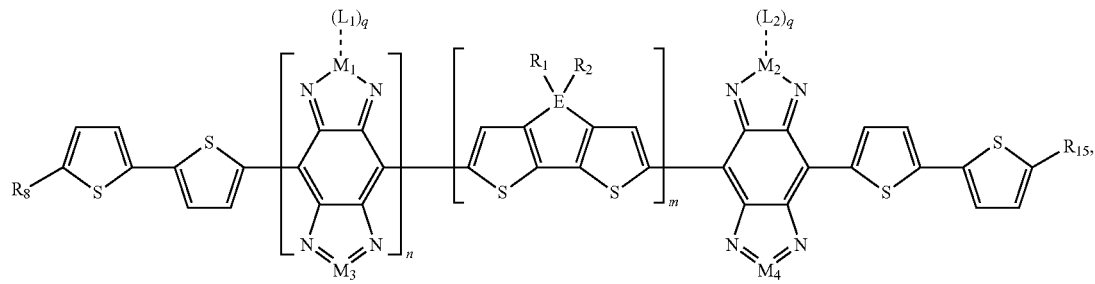

wherein E is C, Si or Ge;

$R_1$ and $R_2$ are each independently a linear, branched or cyclic aliphatic, aryl or heteroaryl group of up to 20 carbon atoms;

$R_8$ and $R_{15}$ are each independently H, a linear, branched or cyclic aliphatic, aryl or heteroaryl group of up to 20 carbon atoms;

$M_1$, $M_2$ and $M_4$ are each independently Se or Te;

$L_1$ and $L_2$ are each individually a coordination ligand bound to $M_1$ and $M_2$, respectively, through a coordination bond, with q being an integer from 1 to 4;

n and m are each integers from 1 to 5.

6. An electronic device comprising an organic or hybrid semiconducting or conducting layer or both comprising a compound of claim 1.

7. The electronic device of claim 6, wherein said device is a polymeric organic light-emitting diodes (PLED), a small-molecule organic light-emitting diodes (SM-OLED), an organic integrated circuit (O-ICs), an organic field effect transistor (OFET), an organic thin film transistor (OTFT), an organic solar cell (O-SC), or an organic laser diode (O-laser).

8. The electronic device of claim 6, wherein the organic electronic device is a single layer, bi-layer, or multiple-layer staking or bulk heterojunction layer organic electronic device.

9. A photovoltaic cell comprising an organic or hybrid semiconducting or conducting layer comprising a compound of claim 1.

10. A process for applying an organic or hybrid semiconducting or conducting layer on a substrate or an electrode, wherein the semiconducting or conducting layer comprises a compound of claim 1, the process comprising disposing said semiconducting or conducting layer on said substrate or said electrode.

11. The process of claim 10, wherein the semiconducting layer is photoactive.

12. The process of claim 10, wherein the conducting layer is photoactive.

13. The process of claim 10, wherein the substrate is a rigid substrate.

14. The process of claim 10, wherein the substrate is a flexible substrate.

15. The process of claim 10, wherein the substrate includes an electrode.

16. The process of claim 10, wherein the semiconducting or conducting layer is disposed on the substrate or the electrode by spray coating, ultra sonic spray coating, roll-to-roll coating, drop casting, dip coating, Mayer rod coating, gravure coating, slot die coating, doctor blade coating, spin coating, meniscus coating, transfer printing, ink-jet printing, offset printing or screen printing process.

17. The process of claim 10, wherein the semiconducting or conducting layer is disposed on the substrate or electrode by vacuum deposition or organic vapor phase deposition (OVPD), solution precipitation, organic molecular beam deposition, or vacuum thermal evaporation (VTE).

18. The process of claim 17, wherein the vacuum deposition is vacuum thermal deposition.

19. A compound having the following structure:

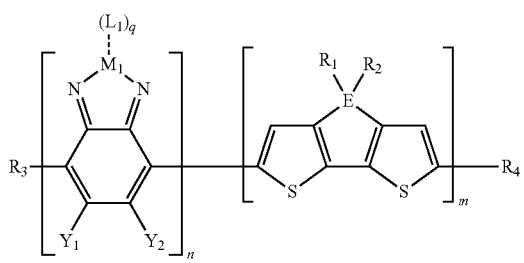

wherein:

E is C, Si, or Ge;

$R_1$ and $R_2$ are each independently a linear, branched or cyclic aliphatic, aryl or heteroaryl group of up to 20 carbon atoms;

$R_3$ is

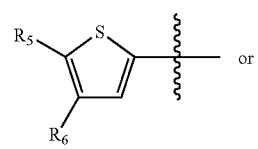

or

-continued

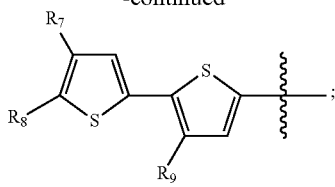

$R_4$ is

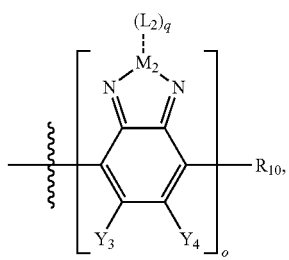

wherein $R_{10}$ is

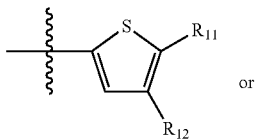 or

-continued

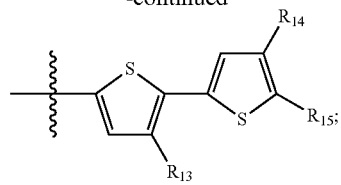

$R_5$, $R_6$, $R_7$, $R_8$, $R_9$, $R_{11}$, $R_{12}$, $R_{13}$, $R_{14}$, and $R_{15}$ are each independently H, a linear, branched or cyclic aliphatic, aryl or heteroaryl group of up to 20 carbon atoms, with the proviso that both of $R_5$ and $R_6$ are not H, both of $R_7$ and $R_8$ are not H, both of $R_{11}$ and $R_{12}$ are not H, and both of $R_{14}$ and $R_{15}$ are not H;

$M_1$ and $M_2$ are Te;

$L_1$ and $L_2$ are each individually a coordination ligand bound to $M_1$ and $M_2$, respectively, through a coordination bond, with q being an integer from 0 to 4;

$Y_1$ and $Y_2$ or $Y_3$ and $Y_4$ are each N and are connected by a metal bridge atom to form, together with the carbon atoms to which they are attached, a 5 member ring system;

n and m are each integers from 1 to 5; and o is an integer from 0 to 5, with the proviso that when o is 0, then $R_4$ is either $R_3$ or an aromatic, heteroaromatic, or alkyl functional group.

20. The compound of claim 19, wherein $Y_1$ and $Y_2$ and $Y_3$ and $Y_4$ are each N and are connected by a metal bridge atom to form, together with the carbon atoms to which they are attached, a 5 member ring system.

* * * * *

UNITED STATES PATENT AND TRADEMARK OFFICE
CERTIFICATE OF CORRECTION

PATENT NO. : 9,543,529 B2
APPLICATION NO. : 14/912253
DATED : January 10, 2017
INVENTOR(S) : S. M. Ibrahim Al-Rafia et al.

Page 1 of 1

It is certified that error appears in the above-identified patent and that said Letters Patent is hereby corrected as shown below:

In the Claims

In Claim 5 on Column 29, Line 35, insert -- ,$M_3$ -- between "$M_2$" and "and $M_4$".

Signed and Sealed this
Eleventh Day of April, 2017

Michelle K. Lee
*Director of the United States Patent and Trademark Office*